(12) United States Patent
Kissinger et al.

(10) Patent No.: US 6,486,222 B2
(45) Date of Patent: Nov. 26, 2002

(54) COMBINATION ION EXCHANGE RESIN BED FOR THE SYNTHESIS OF BISPHENOL A

(75) Inventors: Gaylord M. Kissinger, Evansville, IN (US); Sheldon J. Shafer, Clifton Park, NY (US); Harish R. Acharya, Clifton Park, NY (US); Rudy Francois Alain J. Peemans, Erps-Kwerps (BE); Eduard H. Schlarmann, Bergen op Zoom (NL)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 09/828,721

(22) Filed: Apr. 9, 2001

(65) Prior Publication Data

US 2002/0147241 A1 Oct. 10, 2002

Related U.S. Application Data

(63) Continuation-in-part of application No. 09/258,235, filed on Feb. 26, 1999, now abandoned.

(51) Int. Cl.[7] .............................. B01J 47/02; B01J 39/08
(52) U.S. Cl. .......................... 521/28; 521/33; 568/727; 568/728; 568/723
(58) Field of Search ................................. 568/727, 728; 521/28, 33

(56) References Cited

U.S. PATENT DOCUMENTS

| | | | |
|---|---|---|---|
| 3,394,089 | A | 7/1968 | McNutt et al. |
| 4,051,079 | A | 9/1977 | Melby |
| 4,391,997 | A | 7/1983 | Mendiratta |
| 4,400,555 | A | 8/1983 | Mendriatta |
| 4,590,303 | A | 5/1986 | Mendriatta |
| 5,212,206 | A | 5/1993 | Rudolph et al. |
| 5,284,981 | A | 2/1994 | Rudolph et al. |
| 5,395,857 | A | 3/1995 | Berg et al. |
| 5,455,282 | A | 10/1995 | Berg et al. |
| 5,723,691 | A | 3/1998 | Cipullo et al. |

FOREIGN PATENT DOCUMENTS

| | | |
|---|---|---|
| DE | 3619450 | 12/1987 |
| EP | 210366 | 2/1987 |
| JP | 05 097741 | 4/1993 |

OTHER PUBLICATIONS

F. Helfferich, Ion Exchange, (1962), 546–7, McGraw–Hill (New York).

Primary Examiner—Fred Zitomer

(57) ABSTRACT

The invention is a catalytic ion exchange resin bed with low pressure drop, low catalyst breakage and low catalyst deactivation as well as an improved process for the production of bisphenol A employing such a catalytic ion exchange resin bed.

7 Claims, No Drawings

COMBINATION ION EXCHANGE RESIN BED FOR THE SYNTHESIS OF BISPHENOL A

This application is a continuation-in-part of patent application Ser. No. 09/258,235 filed on Feb. 26, 1999 now abandoned.

BACKGROUND OF THE INVENTION

This invention relates to a process for fixed-bed reactors in the production of bisphenol A, sometimes hereinafter referred to as BPA, which employs a catalytic combination ion exchange resin bed with low pressure drop, low catalyst breakage and long catalyst life.

Processes for the synthesis of bisphenol A by ion exchange resin catalysis are known (see, for example, U.S. Pat. Nos. 4,051,079, 4,391,997, 4,400,555, 4,590,303, 5,395,857, JP-A 8 272 972, EP-A 210 366, etc.).

It is known that, in the industrial production of bisphenol A (BPA), a mixture of excess phenol and acetone is passed through a cylindrical fixed-bed reactor filled with divinyl benzene cross-linked sulfonated polystyrene ion exchange resin catalyst. The direction of flow of the mixture may be either downwards or upwards as required. Each of these feed directions has advantages and disadvantages. Where the feed direction is downwards, the pressure loss through the ion exchange bed is a major problem on account of the resulting compressibility of the ion exchange resin used. The spherical resin particles can be deformed under pressure into a lenticular shape, thus leading to an exponential reduction in throughput. Firm compression of the catalyst bed can promote the formation of flow channels so that flow through the reactor is not uniform. Accordingly, the quantity of catalyst used as a whole may not be fully utilized.

A process has now been found in which the catalyst breakage and deactivation rate in the industrial production of bisphenol A from acetone and phenol in a cylindrical fixed-bed reactor filled with sulfonic acid ion exchange resin catalysts in large quantities can be greatly reduced. Because of the reduction of catalyst resin bead breakage and the substantially lowered rate of catalyst deactivation, the catalyst bed requires less frequent changeovers minimizing lost production time while, at the same time, maintaining efficient pressure drop levels.

Hydraulic problems of the type in question have been observed in particular with ion exchange resin catalysts having a low degree of crosslinking (i.e., less than 2%). On the other hand, these very ion exchange resin catalysts represent an optimum in regard to catalyst bead integrity, reactivity, selectivity and maintenance of catalyst activity in the synthesis of bisphenol A.

Although, with ion exchange resin catalysts having a higher degree of crosslinking (i.e. greater than 2% up to about 4%), the hydraulic problems of the low degree of crosslink resin beds decrease with increasing degree of crosslinking, the friability and deactivation rate of such catalysts in the synthesis of BPA also decrease catalyst life to a considerable extent.

The effect of a higher degree of cross-linked catalyst in BPA synthesis is most pronounced in the catalyst at the portion of the resin catalyst bed which makes up the upper layer of the resin catalyst bed and which is initially in contact with the full force of the reactant mixture as it enters the resin catalyst bed. It has been observed that, the catalyst beads with a higher degree of cross-linking, i.e., greater than 2% to about 4%, which are at the top of the bed (downstream case), break to a large extent within a very short period of operation of the resin catalyst bed. This breakage then leads to extremely high pressure drops because the fractured particles clog the flow channels through the bed and severely impede its efficient operation.

On the other hand, catalyst beads with a low degree of cross-linking, i.e., 2% or less, and high intrinsic flexibility when making up the upper layer of the resin catalyst bed which is initially in contact with the full force of the reactant mixture as it enters the resin catalyst bed withstand the force of the reactant mixture influx, do not show perceptible breakage and do not clog the flow channels so that the efficiency of the resin catalyst bed is maintained and the life of the resin catalyst bed is substantially extended.

One way of improving the hydraulic quality of lightly crosslinked resin beds is to cover some of the sulfonic acid groups with cations. Partial covering with —$NH_3CH_2CH_2SH$ or similar systems, as described for example in DE-A 3 619 450 and U.S. Pat. No. 3,394,089, is particularly advantageous. In addition to embrittlement and hence greater rigidity of the ion exchange resin, a catalytic effect of the groups in the synthesis of BPA is also observed. However, the useful life of such systems is shortened by a factor of approximately 10 compared with unmodified resin systems by deactivation of the co-catalytic unit and is therefore uneconomical. The necessary subsequent regeneration of the large quantities of the sulfonated divinylbenzene cross-linked resin catalyst is time-consuming and expensive and has to be replaced by an equally large quantity of fresh ion exchange resin to maintain the output of BPA.

A resin catalyst bed meeting the long felt need for a catalytic combination ion exchange resin bed with low pressure drop, low catalyst breakage and long catalyst life has now been found. The desirable characteristics of low breakage, less clogging and long catalyst life are found with both attached promoter catalysts as well as bulk promoted catalysts. Further, the shock absorbing layer of ion exchange resin catalyst with a low degree of cross-linking, i.e., 2% or less, causes a rapid reaction of a high percentage of acetone fed into the catalyst bed, thus, substantially reducing the formation of harmful tars and precursors which block the reactive sites on the ion exchange resin catalyst with a higher degree of crosslinking, i.e., greater than 2% to about 4%. This enables the more rigid ion exchange resin catalyst with a higher degree of crosslinking to continue to perform without loss of efficiency for a longer period of time because of the reduction or elimination of tar build up.

SUMMARY OF THE INVENTION

The ion exchange bed for producing bisphenol A from phenol and acetone in a fixed bed reactor containing a gel-form or macroporous sulfonic acid ion exchange resin catalyst bed of the present invention is a resin catalyst bed having an upper layer and a lower layer wherein:

the lower layer comprises a resin which has a higher degree of crosslinking than the upper layer, preferably greater than 2%, more preferably, from greater than 2% to about 4%, and which comprises from 50 to 95%, preferably, from 75 to 85%, of the bed volume as a whole and the upper layer of the bed, which comprises from 5 to 50%, preferably, from 15 to 25%, of the bed volume as a whole, comprises either an unmodified resin having a low degree of crosslinking, preferably 2% or less, or a resin having a low degree of crosslinking, preferably 2% or less, in which 1 to 35 mol % of the sulfonic acid groups are covered with species containing alkyl-SH groups by ionic fixing.

DETAILED DESCRIPTION OF INVENTION

The process for preparing bisphenol A from phenol and acetone in a fixed bed reactor containing gel-form or macroporous sulfonic acid ion exchange resins in the form of a resin catalyst bed of the present invention comprises a process passing a mixture of phenol and acetone through a resin catalyst bed having an upper layer and a lower layer wherein:

the lower layer comprises a resin which has a higher degree of crosslinking than the upper layer, preferably greater than 2%, more preferably, from greater than 2% to about 4%, and which comprises from 50 to 95%, preferably, from 75 to 85%, of the bed volume as a whole and the upper layer of the bed, which comprises from 5 to 50%, preferably, from 15 to 25% of the bed volume as a whole, comprises either an unmodified resin having a low degree of crosslinking, preferably 2% or less, or a resin having a low degree of crosslinking, preferably 2% or less, in which 1 to 35 mol % of the sulfonic acid groups are covered with species containing alkyl-SH groups by ionic fixing.

In a preferred embodiment, the lower layer of the ion exchange bed has a degree of crosslinking from equal to or greater than 2% to less than or equal to 4%.

In another preferred embodiment, the lower layer of the ion exchange bed is a resin in which from 1 to 25 mol % of the sulfonic acid groups are covered with species containing alkyl-SH groups by ionic fixing In still another preferred embodiment, the upper layer of the ion exchange bed has a degree of crosslinking less than or equal to 2%. This upper layer is either an unmodified resin or a resin in which from 1 to 35 mol % of the sulfonic acid groups are covered with species containing alkyl-SH groups by ionic fixing.

Ionic fixing is described in DE-A 3 619 450 or in U.S. Pat. No. 3,394,089.

In the practice of the process of the present invention, it is preferred that the flow of acetone and phenol proceed from above the bed down through the bed. This is the flow pattern conventionally used in the process for making BPA. However, if for any reason it is desired to reverse the flow of the phenol and acetone through the bed, i.e., pass the phenol and acetone up through the bed from the bottom, the benefits of longer bed life, lower catalyst breakage and high yields of BPA can still be achieved merely by reversing the layers so that the resin with the lower cross-link density is on the bottom and the resin with higher cross-link density is on the top. The key is to have the resin with the lower cross-link density cover the surface of the bed through which the phenol and acetone enter the bed to minimize catalyst breakage by absorbing the impact of the full force of the incoming phenol and acetone mixture. Thus, in the description of the present invention it is intended that the upper layer be construed as the layer through which the phenol and acetone mixture enters the resin catalyst bed and the lower layer be construed as the layer through which the reacted mixture exits the resin catalyst bed.

It has been surprisingly found that employing as the upper layer of the resin catalyst bed a resin with a lower degree of cross-linking and as the lower layer of the resin catalyst bed a resin with a higher degree of cross-linking, resin catalyst bed life is extended because catalyst fouling and deactivation and fracturing of the catalyst resin beads are reduced. Further, employing the resin with a higher degree of cross-linking in a preferred embodiment of the present invention as the major component of the resin catalyst bed, provides increased yields of BPA at high production rates.

From the hydraulic point of view, resin beds according to the invention behave as if the lower rigid resin layer were the sole filling of the reactor, i.e. the capacity of the reactor is no longer determined by the hydraulics of the filling, but instead by the acetone conversion which proceeds at a particularly high rate of reaction in the lower crosslinked top layer of the catalyst resin bed.

In addition to its favorable hydraulic properties in the synthesis of BPA, the two layer combination bed of the present invention surprisingly shows the excellent reactivity and selectivity behavior of a resin bed entirely consisting of a lightly crosslinked ion exchange resin type, having a cross-link density of equal to or less than 2%.

In a preferred embodiment of the process of the present invention, a mixture of phenol, recycled mother liquor (consisting of phenol, bisphenol A and secondary products) and acetone is introduced into the reactor from above through a pipe. The reactor is normally filled with ion exchange resin to between 50 and 80% of its total volume. The water-wet ion exchange resin catalyst can be dried or partially dried prior to charging it to the reactor, the advantage being that dried or partially dried ion exchange resin catalyst shrinks during the drying stage and does not shrink during dehydration with phenolic compounds. Hence, more ion exchange resin catalyst can be charged in the reactor and the 2 catalyst layers will not being disturbed during the dehydration stage.

In the lower part of the reactor, there is a layer of mineral material as carrier for the resin bed. The reaction mixture flows downwards through the fixed bed. The reaction solution exits from the reactor at its lower end and is then subjected to further processing.

The feed volume is normally controlled by a pneumatic control valve and a through flow meter. The feed temperature is in the range from 50° C. to 62° C.; the discharge temperature is in the range from 75° C. to 85° C. The reactor is operated under adiabatic conditions. Heat losses are avoided by insulation and backup heating. The pressure loss through the resin catalyst bed is measured in the upper part of the reactor. For safety reasons, introduction of the reaction mixture is stopped when the pressure loss caused by the resin catalyst bed reaches 2 bar.

The composition by weight of the reaction mixture introduced into the reactor may vary within the following limits: phenol 75–85% by weight, bisphenol A and secondary products 12–20% by weight and acetone 2–6% by weight.

In a preferred embodiment of the present invention the catalyst bed is treated more delicately during start-up to avoid breakage of the catalyst. A reactor feed during normal steady state conditions will typically contain up to 5% acetone and 6000 ppm of 3-mercaptopropionic acid (3-mpa) with phenol. During the first week of catalyst start up it is preferred to start with a low acetone concentration and slowly increase it to 4% (e.g., steps of 0.1% every 2 hours). During the next 1 or 2 weeks it is best to keep the acetone concentration at 4%. Next, the acetone concentration can be increased to 4.2%. After operation at 4.2% for 1–4 weeks, the concentration can be slowly increased to 4.5%. After another 1–4 weeks the concentration may be slowly increased to 5%. If this careful start up procedure is used it is possible to significantly extend catalyst life.

EXAMPLE 1

(Comparison)

A BPA reactor, was charged resin sulfonated polystyrene (4% cross-linked with divinylbenzene) with ion exchange catalyst At a reactor feed rate of 1.0 WHSV, a temperature of 58° C., a pressure drop of 0.65 bar and a conversion of 96% was observed. Using a 1.3 WHV feed rate, the pressure drop increased to 1.1 bar.

EXAMPLE 2

The same BPA reactor as employed in Example 1 was charged with an equal weight of catalyst as in Example 1, 90% by weight (on a dry basis) of a sulfonated polystyrene (4% cross-linked with divinylbenzene) catalyst (same bead size as in Example 1) as a lower layer of the resin catalyst bed and 10% by weight (on dry basis) of a sulfonated polystyrene (2% cross-linked with divinylbenzene) catalyst were charged to the reactor as the upper layer of the resin catalyst bed. Surprisingly, the pressure drop neither increased nor decreased due to the upper layer of 2% catalyst. Using the same feed and temperature conditions as described in example 1, and a feed rate of 1.0 WHSV hour, a pressure drop of only 0.67 bar was observed. At a 1.3 WHSV feed rate, all other conditions the same, the pressure increased to 1.1 bar.

EXAMPLE 3

(Comparison)

The ion exchange resin catalyst bed of Example 1 was simulated in a laboratory scale reactor to illustrate the effect of the direct impact of the BPA feedstock on a ion exchange resin bed with a top layer of 4% crosslinked resin beads. 5 grams of commercially available 4% cross-linked ion exchange resin catalyst was charged to the laboratory reactor. A feed mixture typical of feeds employed in the commercial manufacture of bisphenol-A containing 77% by weight of phenol, 6% by weight acetone and 17% by weight of bisphenol-A and other compounds present in bisphenol-A plant recycle streams was charged to the reactor in the downflow mode at 70° C. and a WHSV of 10 for a period of 16 days. The conversion on the first day was 4.2 grams per hour. The conversion on the 16th day was 3.4 grams per hour.

EXAMPLE 4

The ion exchange resin catalyst bed of the present invention was simulated in a laboratory scale reactor to illustrate the improved BPA catalyst performance because of reduced ion exchange resin catalyst bead breakage and catalyst fouling resulting from the direct impact of the BPA feedstock on an ion exchange resin bed with a top layer of 2% crosslinked resin beads in accordance with the present invention. 2.5 grams of commercially available 2% cross-linked ion exchange resin catalyst was charged to the laboratory reactor on top of 2.5 grams of commercially available 4% cross-linked catalyst previously charged to the laboratory reactor. A feed mixture typical of feeds employed in the commercial manufacture of bisphenol-A containing 77% by weight of phenol, 6% by weight acetone and 17% by weight of bisphenol-A and other compounds present in bisphenol-A plant recycle streams was charged to the reactor in the downflow mode at 70° C. and a WHSV of 10 for a period of 16 days. The conversion on the first day was 4.74 grams per hour The conversion on the 16th day was 4.59 grams per hour.

What is claimed is:

1. In an ion exchange bed for producing bisphenol A from phenol and acetone in a fixed bed reactor containing a gel-form or macroporous sulfonic acid ion exchange resin catalyst bed, the improvement comprising a resin catalyst bed having an upper layer and a lower layer wherein:

the lower layer comprises a resin which has a higher degree of crosslinking than the upper layer and which comprises 50 to 95% of the bed volume as a whole and the upper layer of the bed, which comprises 5 to 50% of the bed volume as a whole, comprises either an unmodified resin having a low degree of crosslinking or a resin having a low degree of crosslinking in which 1 to 35 mol % of the sulfonic acid groups are covered with species containing alkyl-SH groups by ionic fixing.

2. The ion exchange bed of claim 1 wherein the lower layer has a degree of crosslinking from equal to or greater than 2% to less than or equal to 4%.

3. The ion exchange bed of claim 2 wherein the lower layer is a resin in which 1 to 25 mol % of the sulfonic acid groups are covered with species containing alkyl-SH groups by ionic fixing.

4. The ion exchange bed of claim 1 wherein the upper layer has a degree of crosslinking less than or equal to 2%.

5. The ion exchange bed of claim 4 wherein the upper layer is an unmodified resin.

6. The ion exchange bed of claim 4 wherein the upper layer is a resin in which 1 to 25 mol % of the sulfonic acid groups are covered with species containing alkyl-SH groups by ionic fixing.

7. The ion exchange bed of claim 1 wherein the lower layer comprises 75 to 85% of the bed volume as a whole and the upper layer comprises 15 to 25% of the bed volume as a whole.

* * * * *